United States Patent [19]

Masuda et al.

[11] 4,327,183

[45] Apr. 27, 1982

[54] METHOD FOR PURIFYING FATTY ACID ESTERS OF SACCHARIDE

[75] Inventors: Takayoshi Masuda; Masaru Honjo; Tsutomu Takase; Yoshimoto Watanabe, all of Nagoya, Japan

[73] Assignee: Mitsui Toatsu Chemicals, Inc., Tokyo, Japan

[21] Appl. No.: 198,009

[22] PCT Filed: Apr. 3, 1979

[86] PCT No.: PCT/JP80/00059
§ 371 Date: Dec. 5, 1981
§ 102(e) Date: Oct. 17, 1980

[87] PCT Pub. No.: WO80/02156
PCT Pub. Date: Oct. 16, 1980

[30] Foreign Application Priority Data

Apr. 5, 1979 [JP] Japan .................. 54/40378
Apr. 5, 1979 [JP] Japan .................. 54/40379

[51] Int. Cl.$^3$ .................................. C07H 13/02
[52] U.S. Cl. .................... 435/274; 435/276; 536/119
[58] Field of Search .......... 536/116, 119; 435/274, 435/276

[56] References Cited

U.S. PATENT DOCUMENTS 3,058,887 10/1962 Platt et al. .................. 435/271
3,249,600  5/1966 Nobile et al. ................ 536/119

FOREIGN PATENT DOCUMENTS 46-269  of 1971 Japan .
50-25743 of 1975 Japan .

OTHER PUBLICATIONS

Tamate et al., "Sucrose Esters of Long Chain Fatty Acids", Yukaguku (Oil Chemistry), vol. 16, No. 7 (1967), pp. 395–401.
Chemical Abstract 13285(a), vol. 68 (1968).

Primary Examiner—John F. Niebling
Attorney, Agent, or Firm—Fisher, Christen & Sabol

[57] ABSTRACT

This invention provides a method for purifying crude fatty acid esters of saccharide containing at least fatty acid glycerides as impurity, and which method comprises decomposing the fatty acid glycerides by the treatment thereof with a lipid splitting enzyme or with a combination of a lipid splitting enzyme and a reducing agent in the presence of water.

9 Claims, No Drawings

METHOD FOR PURIFYING FATTY ACID ESTERS OF SACCHARIDE

TECHNICAL FIELD

This invention relates to a method for purifying fatty acid esters, and more particularly relates to a method for purifying fatty acid esters of saccharide, which method comprises removing fatty acid glycerides from crude fatty acid esters of saccharide containing at least fatty acid glycerides as impurity for the purification thereof.

BACKGROUND ART

Fatty acid esters of saccharide are very useful compounds such that they are finding their wide applications such as additives for food, cosmetics, drugs, resins, etc., detergents for clothing, detergents for the kitchen, shampoos, and the like as a surface-active agent which can fundamentally solve such problems as environmental pollution, toxicity for living organisms, and the like because of their high biodegradability and safety.

The preferred processes for preparing fatty acid esters of saccharide among those known in the art include one according to alcoholysis of saccharide with fatty acid lower alkyl esters, and one according to alcoholysis of saccharide with fats and fatty acids, that is, fatty acid triglyceride.

Especially, the latter process has great advantages as a process for preparing fatty acid esters of saccharide, because the process generally makes it possible to directly use relatively cheap animal and plant fats and oils such as beef tallow, palm oil, coconut oil and the like as starting material. The reaction product obtained by the above process contains fatty acid glycerides, which are usually a mixture of unreacted fatty acid triglyceride, fatty acid diglyceride and fatty acid monoglyceride, soap, and unreacted free saccharide besides fatty acid esters of saccharide, and these impurities are required to be removed therefrom in order to purify the fatty acid esters of saccharide.

Among these impurities, the soap and free saccharide can be almost completely removed easily and without substantial loss of fatty acid esters of saccharide according to a process by the application of the conversion to their derivatives, difference in their solubilities in solvent, or the like.

On the other hand, according to a method known in the art for removing fatty acid glycerides, a solid-liquid extraction is effected by the use of an organic solvent such as acetic esters, ketones, and the like to remove the fatty acid glycerides. Difference in solubility in an organic solvent between fatty acid esters of saccharide, especially fatty acid polyesters of saccharide having two or more ester linkages in one molecule and fatty acid glycerides is so small that it is extremely difficult for the former to be separated completely from the latter. Therefore, the conventional methods mentioned above have such serious defects that the complete removal of fatty acid glycerides causes a high loss of fatty acid esters of saccharide.

Accordingly, it is an object of the present invention to provide a novel method for purifying fatty acid esters of saccharide in order to overcome the above defects due to the conventional processes.

DISCLOSURE OF THE INVENTION

The present invention provides a method for purifying fatty acid esters of saccharide, which method comprises treating crude fatty acid esters of saccharide containing at least fatty acid glycerides as impurity with a lipid splitting enzyme, or with a combination of a lipid slitting enzyme and a reducing agent in the presence of water to decompose the fatty acid glycerides therein.

BEST EXPLOITATION MODE OF THE INVENTION

The present invention is further described in detail.

The fatty acid esters of saccharide of the present invention include any fatty acid esters of saccharide which are esters of monosaccharide such as arabinose, xylose, ribose, glucose (grape sugar), mannose, galactose, fructose (fruit sugar), maltose (malt sugar), cellobiose, trehalose, gentiobiose, isomaltose, lactose (milk sugar), sucrose (cane sugar), raffinose, gentianose, maltotriose, stachyose, xylan, araban, cellulose, starch and the like, disaccharide, trisaccharide, tetrasaccharide, or polysaccharide with a fatty acid having 6 to 24 carbon atoms, and have at least one ester linkage in one molecule. Especially, the fatty acid esters of cane sugar are one of the fatty acid esters of saccharide most preferably applicable to the method of the present invention.

The fatty acid glycerides include either one of fatty acid triglyceride, fatty acid diglyceride or fatty acid monoglyceride derived from a fatty acid having 6 to 24 carbon atoms, or a mixture thereof.

The crude fatty acid esters of saccharide, to which the method of the present invention is applicable, contain as impurity at least fatty acid glycerides mentioned above, and may further include soaps such as sodium soap, potassium soap, amine soap, calcium soap, and the like, free fatty acids, free saccharide, glycerin, inorganic salts, etc.

The crude fatty acid esters of saccharide are dissolved or suspended in water by adding water thereto directly or after removing partially or totally coexisting soaps, free saccharide, etc.

The amount of water to be added is preferred to be such that the concentration of crude fatty acid esters of saccharide is usually in the range of from 1 to 90% by weight, preferably from 5 to 70% by weight, more preferably from 10 to 50% by weight. Too much water added unfavorably needs such a large amount of energy as to be uneconomical, in order to remove water thereafter, and too little water added also unfavorably causes viscosity increase of an aqueous solution of crude fatty acid esters of saccharide for leading to incomplete mixing thereof with a lipid splitting enzyme and a reducing agent, which makes it difficult to provide a sufficient effect of the present invention.

The typical example of the lipid splitting enzyme includes acylglycerol lipase and specific examples thereof include Rhizopus acylglycerol lipase, Aspergillus acylglycerol lipase, Mucor acylglycerol lipase, Pseudomonas acylglycerol lipase, Candida acylglycerol lipase, Pancreas acylglycerol lipase, and the like. The lipid splitting enzyme used is not always necessary to be a purified acylglycerol lipase, but may be any acylglycerol lipase which has a lipid splitting activity and does not cause decomposition of fatty acid esters of saccharide.

Specific examples of the reducing agent include sodium dithionite, vitamin C, glutathione, 2-mercaptoethanol, sodium sulfite, sodium thiosulfate, hydroquinone, and the like.

The lipid splitting enzyme and reducing agent are added directly or after dissolving in water etc. to an aqueous solution or suspension of crude fatty acid esters of saccharide containing at least fatty acid glycerides mentioned above.

In the decomposition of fatty acid glycerides contained in the crude fatty acid esters of saccharide by the treatment thereof with a lipid splitting enzyme, or with a reducing agent along therewith, pH and temperature are of the greatest importance. The value of pH depends on the kind of the lipid splitting enzyme, but is preferred to be adjusted usually in the range of from 2 to 10, preferably from 3 to 9.5, and more preferably from 4 to 9. The pH adjustor used includes conventional acids, alkalis, salts, and the like. The temperature is preferred to be maintained usually in the range of from 10° to 70° C., preferably from 20° to 60° C., and more preferably from 25° to 50° C.

In the case where the pH and temperature are out of the ranges mentioned above, the action of the lipid splitting enzyme is unfavorably inhibited, and further the hydrolytic reaction of the fatty acid esters of saccharide themselves in the presence of an acid base catalyst is also unfavorably promoted at a high temperature and under a strongly acidic or alkaline condition.

The amount to be used of the lipid splitting enzyme or the reducing agent varies with the content of fatty acid glycerides in the crude fatty acid esters of saccharide, the strength of lipid splitting enzyme itself, etc. However, the amount to be used of lipid splitting enzyme is in the range of from 0.0001 to 20% by weight based on the crude fatty acid esters of saccharide, preferably 0.0005 to 10% by weight, more preferably from 0.001 to 5% by weight, and the amount to be used of the reducing agent is in the range of from 0.000001 to 0.2% by weight based on the crude fatty acid esters of saccharide, preferably from 0.000005 to 0.1% by weight, and more preferably from 0.00001 to 0.05% by weight. The amount to be used less than the above lower limit of the lipid splitting enzyme or the reducing agent unfavorably makes it difficult to provide a sufficient effect of the present invention, and the amount to be used more than the upper limit mentioned above is unfavorably uneconomical.

The time required for the decomposition of the fatty acid glycerides contained in the crude fatty acid esters of saccharide with the lipid splitting enzyme is usually in the range of from 1 to 100 hours, preferably 3 to 70 hours, and more preferably 5 to 50 hours.

When a reducing agent is employed along with the lipid splitting enzyme, however, the time mentioned above is usually in the range of from 30 minutes to 50 hours, preferably 1 to 40 hours, and more preferably 3 to 30 hours.

A major portion or almost all of the fatty acid glycerides contained in the crude fatty acid esters of saccharide is finally decomposed into free fatty acid and glycerin by the application of preferred decomposition conditions above mentioned with a lipid splitting enzyme only or preferably with a combination thereof with a reducing agent.

After the decomposition of fatty acid glycerides, highly purified fatty acid esters of saccharide can readily be obtained by the application thereto of an appropriate combination of conventional purifying methods such as filtration, conversion of free fatty acids into other derivatives, solvent extraction, recrystallization, and the like.

As described in detail as above, in accordance with the method of the present invention, the fatty acid glycerides contained in the crude fatty acid esters of saccharide containing at least fatty acid glycerides as impurity can be selectively decomposed into free fatty acid and glycerin which can readily be separated from each other, and, moreover, the loss of the fatty acid esters of saccharide can be substantially prevented, which results in providing a method for purifying fatty acid esters of saccharide which is highly advantageous from an industrial viewpoint.

The present invention will be further illustrated in detail by the following examples.

EXAMPLE 1

To a mixed solution of 20 g of coconut oil fatty acid ester of cane sugar, 10 g of triaurin (glycerol trilaurate), and 70 g of water, a dilute aqueous acetic acid was added drop by drop to adjust pH to 5.5, and then 0.05 g of [Aspergillus] lipase AP4 was added thereto. The resultant mixture was treated for 30 hours with agitation in a constant temperature bath at 35° C.

A portion of the treated solution was carefully sampled and lauric acid thus formed was subjected to quantitative analysis (a blank test was effected simultaneously) by means of neutralization titration method which alcoholic standard solution of potassium hydroxide by use of phenolphthalein as a neutralization indicator with the result that 97% of trilaurin originally used was hydrolyzed to lauric acid.

Another part of the treated solution as above, which was sampled separately from the above, was subjected to quantitative analysis by means of gas chromatography with the result that no coconut oil fatty acid ester of cane sugar was decomposed.

EXAMPLE 2

To a mixed solution of 7 g of hydrogenated beef tallow fatty acid ester of cane sugar, 3 g of distearin (glycerol distearate), and 90 g of water, 0.005 g of [Aspergillus] lipase M-AP10 was added. The resultant mixture was treated at 35° C. for 30 hours in the same manner as in Example 1, and the treated solution was subjected to quantitative analysis with the result that 98% of distearin was hydrolyzed to stearic acid and that no hydrogenated beef tallow fatty acid ester of cane sugar was decomposed.

EXAMPLE 3

To a mixed solution (pH 9.2) of 10 g of monopalmitate of cane sugar, 5 g of dipalmitate of cane sugar, 5 g of palm oil (saponification value: 198 mg KOH/g), 5 g of potassium palmitate, and 75 g of water, 0.10 g of [Aspergillus] pancreatin was added, and the resultant mixture was treated with agitation in a constant temperature bath at 30° C. for 48 hours and then was subjected to analysis with the result that 72% of palm oil originally added was hydrolyzed to the corresponding fatty acid and that neither monopalmitate of cane sugar nor dipalmitate of cane sugar was decomposed.

EXAMPLE 4

To a mixed solution of 10.5 g of monolaurate of cane sugar, 4.5 g of dilaurate of cane sugar, 3 g of monolaurin (glycerol monolaurate), 2 g of dilaurin (glycerol dilaurate), 15 g of potassium laurate, and 65 g of water, acetic acid was added drop by drop to adjust pH to 8, and then 0.020 g of pancreatin and 0.005 g of lipase M-AP10 were added thereto. The resultant mixture was treated in a constant temperature bath at 40° C. for 24 hours, and then subjected to analysis with the result that 95% of monolaurin and all of dilaurin were hydrolyzed to lauric acid respectively, and that neither monolaurate of cane sugar nor dilaurate of cane sugar was decomposed.

EXAMPLE 5

Acetic acid was added dropwise to a mixture of 35 g of crude fatty acid esters of cane sugar, which were composed of 20% of fatty acid monoester of cane sugar, 9% of fatty acid diester of cane sugar, 10% of fatty acid monoglyceride, 10% of fatty acid diglyceride, 4% of fatty acid triglyceride, 30% of potassium soap, and 17% of free cane sugar, and which were obtained by alcoholysis of cane sugar with beef tallow in the presence of potassium carbonate as catalyst, and 65 g of water to adjust pH to 7.5, and then 0.021 g of lipase M-AP10 was added thereto. The resultant mixture was treated with agitation in a constant temperature bath at 40° C. for 20 hours. Aqueous potassium hydroxide was added to the treated solution as above to convert fatty acid therein into potassium soap, and then calcium chloride was added thereto to convert the potassium soap into calcium soap. The major portion of water therein was distilled off under reduced pressure to form a wet cake, which was subjected to extraction with 100 ml of isopropanol. The same extraction procedure as above was repeated once more, and the resultant isopropanol extract solution was concentrated under reduced pressure to obtain 10.4 g of solid matter, which was subjected to composition analysis thereof with gas chromatography and liquid chromatography with the result that the resultant solid matter contained 66% of fatty acid monoester of cane sugar, 29% of fatty acid diester of cane sugar, 1% of free cane sugar, 3% of fatty acid monoglyceride, and 1% of fatty acid diglyceride, and that the total purity of fatty acid esters of cane sugar (monoester + diester) was 95%.

The yields for purification of fatty acid monoester of cane sugar and fatty acid diester of cane sugar can be calculated from the above results to be 98.1% and 95.7%, respectively.

EXAMPLE 6

To a mixture of 40 g of crude fatty acid esters of cane sugar, which were composed of 25% of fatty acid monoester of cane sugar, 10% of fatty acid diester of cane sugar, 12% of fatty acid monoglyceride, 8% of fatty acid diglyceride, 2% of fatty acid triglyceride, and 43% of potassium soap, free cane sugar, glycerin, etc., and which were obtained by alcoholysis of cane sugar with coconut oil in the presence of potassium carbonate and potassium hydroxide as catalyst, and 60 g of water, 2.4 g of citric acid was added for adjusting pH to 6, and then 0.08 g of [Aspergillus] lipase P was added thereto. The resultant mixture was treated with agitation in a constant temperature bath at 40° C. for 24 hours. After the treatment was completed, a part of the treated solution as above was sampled for freeze-drying, and subjected to composition analysis thereof with a combination of gas chromatography and liquid chromatography with the result that the treated solution contained 3% of fatty acid monoglyceride, that neither fatty acid diglyceride nor fatty acid triglyceride was recognized, that the content of fatty acid esters of cane sugar therein was such that monoester thereof was 23.5% and diester thereof was 9.4%, and that no fatty acid esters of cane sugar were substantially decomposed taking into consideration the dilution effect due to addition of 2.4 g of citric acid at the time of pH adjustment.

EXAMPLE 7

To a mixed solution of 14 g of monolaurate of cane sugar, 6 g of dilaurate of cane sugar, 10 g of trilaurin (glycerol trilaurate), and 70 g of water, dilute aqueous acetic acid was added dropwise for adjusting pH to 5.5, and then 0.02 g of [Aspergillus] lipase AP4 and 0.4 g of aqueous solution of 0.1% by weight of sodium dithionite were added thereto. The resultant mixture was subjected to decomposition with gentle agitation in a constant temperature bath at 37° C. for 5 hours. A part of the resultant decomposed solution was carefully sampled, and the formed lauric acid was subjected to quantitative analysis (separately a blank test was effected) by means of neutralization titration method with alcoholic standard solution of potassium hydroxide by use of phenolphthalein as a neutralization indication with the result that 96% of trilaurin was hydrolyzed to laurid acid.

Another part of the resultant decomposed solution as above, which was sampled separately from the above, was subjected to quantitative analysis by means of gas chromatography with the result that neither monolaurate of cane sugar nor dilaurate of cane sugar was decomposed.

EXAMPLE 8

To a mixed solution of 6 g of monostearate of cane sugar, 4 g of monoolein (glycerol monooleate), and 90 g of water, 0.004 g of [Aspergillus] lipase M-AP10 and 0.8 g of aqueous solution of 0.01% by weight of vitamin C were added, and the resultant mixture was subjected to decomposition at 37° C. for 5 hours in the same manner as in Example 1. The result of analysis thereof showed that 95% of monoolein was hydrolyzed to oleic acid and no monostearate of cane sugar was decomposed.

EXAMPLE 9

To a mixed solution of 7 g of monostearate of cane sugar, 3 g of beef tallow (saponification value: 192 mg KOH/g), 5 g of potassium oleate, and 85 g of water, dilute aqueous acetic acid solution was added dropwise for adjusting pH to 8, and then 0.06 g of [Aspergillus] pancreatin, 0.006 g of lipase M-AP10, and 0.6 g of aqueous solution of 0.1% by weight of glutathion were added thereto. The resultant mixture was subjected to decomposition with gentle agitation in a constant temperature bath at 40° C. for 2 hours to effect analysis thereof, the result of which showed that 96% of beef tallow was hydrolyzed to the corresponding fatty acid, and no monostearate of cane sugar was decomposed.

EXAMPLE 10

To a mixed solution of 9.0 g of monolaurate of cane sugar, 3.8 g of dilaurate of cane sugar, 3.2 g of monolaurin (glycerol monolaurate), 2.4 g of dilaurin (glycerol dilaurate), 1.2 g of trilaurin (glycerol trilaurate), 14.0 g of potassium laurate, 6.4 g of cane sugar, and 60 g of water, dilute aqueous acetic acid was added dropwise for adjusting the pH to 7.5, and then 0.014 g of lipase M-AP10 and 0.28 g of aqueous solution of 0.1% by weight of mercaptoethanol were added thereto. The resultant mixture was subjected to decomposition with gentle agitation in a constant temperature bath at 30° C. for 5 hours, and then aqueous potassium hydroxide was added to the solution decomposed as above to convert fatty acid therein into potassium soap followed by adding calcium chloride thereto to convert the potassium soap into calcium soap. A major portion of water therein was distilled off under reduced pressure to obtain a wet cake. To the wet cake 200 ml of isopropanol was added for effecting extraction thereof. The isopropanol extract solution was dried with anhydrous sodium sulfate, and then isopropanol was distilled off under reduced pressure to obtain 13.2 g of white solid matter, which was subjected to composition analysis with gas chromatography and liquid chromatography with the result that the solid matter contained 67% of monolaurate of cane sugar, 27% of dilaurate of cane sugar, 1% of free cane sugar, and 5% of monolaurin, and that the total purity of monolaurate of cane sugar and dilaurate of cane sugar was 94%.

The yields for purification of monolaurate of cane sugar and dilaurate of cane sugar can be calculated from the above results to be 98.3% and 93.8%, respectively.

COMPARATIVE EXAMPLE 1

To a mixture of 35 g of the same crude fatty acid ester of cane sugar as in Example 5 and 65 g of water, calcium chloride is added for converting potassium soap to calcium soap, and then major portion of water therein is distilled off under reduced pressure to form a wet cake. The wet cake is subjected to extraction and concentration procedure in the same manner as in Example 5 to obtain a solid matter. To the solid matter 100 ml of ethyl acetate is added for extracting fatty acid glycerides therewith. The same extraction procedure as above is repeated once more, and the resultant ethyl acetate extract solution is concentrated under reduced pressure to obtain 9.7 g of a solid matter, which is subjected to composition analysis with the result that the solid matter contains 63% of fatty acid monoester of cane sugar, 23% of fatty acid diester of cane sugar, 1% of free cane sugar, 10% of fatty acid monoglyceride, and 3% of fatty acid diglyceride, and that the total purity of fatty acid esters of cane sugar (monoester+diester) is 86%.

The yields for purification of fatty acid monoester of cane sugar and fatty acid diester of cane sugar can be calculated from the above results to be 87.3% and 70.8% respectively.

CAPABILITIES OF EXPLOITATION IN INDUSTRY

Application of a method for purifying fatty acid esters of saccharide of the present invention to intermediate products obtained during the steps for the preparation of fatty acid esters of saccharide makes it possible to purify fatty acid esters of saccharide at high purity as well as at high yield.

We claim:

1. A method for purifying crude fatty acid esters of saccharide containing at least fatty acid glycerides as impurity, which method comprises decomposing the fatty acid glycerides by the treatment thereof with a lipid splitting enzyme or with a combination of a lipid splitting enzyme and a reducing agent in the presence of water.

2. The method for purifying according to claim 1, wherein the fatty acid esters of saccharide are fatty acid esters of cane sugar.

3. The method for purifying according to claim 1, wherein the fatty acid glycerides are either one of fatty acid monoglyceride, fatty acid diglyceride or fatty acid triglyceride, or a mixture thereof.

4. The method for purifying according to claim 1, wherein the crude fatty acid esters of saccharide are composed of fatty acid esters of saccharide, fatty acid glycerides, soap, and free saccharide.

5. The method for purifying according to claim 1, wherein the lipid splitting enzyme is acylglycerol lipase.

6. The method for purifying according to claim 1, wherein the reducing agent is sodium dithionite.

7. The method for purifying according to claim 1, wherein the reducing agent is vitamin C.

8. The method for purifying according to claim 1, wherein the reducing agent is glutathione.

9. The method for purifying according to claim 1, wherein the reducing agent is 2-mercaptoethanol.

* * * * *